United States Patent [19]

Ewing et al.

[11] Patent Number: 5,340,801
[45] Date of Patent: Aug. 23, 1994

[54] COMPOUNDS HAVING CHOLECYSTOKININ AND GASTRIN ANTAGONISTIC PROPERTIES

[75] Inventors: William R. Ewing, King of Prussia; Bruce F. Molino, Hatfield, both of Pa.

[73] Assignee: Rhone-Poulenc Rorer Pharmaceuticals Inc., Collegeville, Pa.

[21] Appl. No.: 697,177

[22] Filed: May 8, 1991

[51] Int. Cl.$^5$ .................. A61K 31/40; A61K 37/43; C07K 5/06; C07K 5/08
[52] U.S. Cl. .......................... 514/18; 514/19; 514/210; 514/212; 514/315; 514/410; 514/411; 514/423; 530/330; 530/331; 540/606; 540/607; 546/244; 546/245; 548/492; 548/538
[58] Field of Search .................. 530/332, 331, 330; 514/18, 19, 410, 411, 423, 315, 212, 210; 548/418, 421, 426, 427, 429, 469, 492, 538, 953; 540/606, 607; 546/244, 245

[56] References Cited

U.S. PATENT DOCUMENTS

| | | | |
|---|---|---|---|
| 3,886,177 | 5/1975 | Fontanella et al. | 548/518 |
| 4,357,471 | 11/1982 | Smolanoff | 540/607 |
| 4,559,339 | 12/1985 | Bock et al. | 514/219 |
| 4,684,646 | 8/1987 | Chang et al. | 514/221 |
| 4,692,522 | 9/1987 | Parsons et al. | 540/523 |
| 4,757,068 | 7/1988 | Parsons | 514/213 |
| 4,812,452 | 3/1989 | Shanklin, Jr. et al. | 540/607 |
| 4,820,834 | 4/1989 | Evan et al. | 540/504 |
| 4,847,248 | 7/1989 | Freidinger et al. | 514/214 |
| 4,880,938 | 11/1989 | Freidinger et al. | 548/492 |
| 4,910,190 | 3/1990 | Bergeson et al. | 514/19 |
| 5,075,313 | 12/1991 | Yu et al. | 514/259 |
| 5,162,336 | 11/1992 | Molino et al. | 514/292 |

FOREIGN PATENT DOCUMENTS

| | | |
|---|---|---|
| 166355 | 1/1986 | European Pat. Off. |
| 250148 | 12/1987 | European Pat. Off. |
| 304223 | 2/1989 | European Pat. Off. |
| 450537 | 1/1991 | European Pat. Off. |
| 81857 | 6/1980 | Japan . |
| 00295 | 1/1992 | World Int. Prop. O. |
| 04348 | 3/1992 | World Int. Prop. O. |

OTHER PUBLICATIONS

Eur. J. Pharm., vol. 162 issued 1989, Lotti et al., "A New potent and selective non-peptide gastrin . . . ", pp. 273-280.
PNAS, vol. 78, No. 10, issued Oct. 1981, Hahne et al., "Proglumide and benzotript . . . ", 6304-6308.
J. Med. Chem., vol. 31, issued 1988, Evans et al., "Methods for Drug Discovery . . . ", pp. 2235-2246.
Japan J. Pharmacol., vol. 46, issued 1988, Itonaga et al., "Cholecystokinin Antagonism . . . ", pp. 319-324.
J. Med. Chem., vol. 25, issued 1982, Cain et al., "β-Carbolines: Synthesis and Neurochemical . . . ", pp. 1081-1091.
Heterocycles, vol. 22, No. 1, issued 1984, Coutts et al., "Some 3-Carboxamides of β-Carboline . . . ", p. 131.
U.S. patent application Ser. No. 07/542,295.
U.S. patent application Ser. No. 07/573,514.
Chemical Abstract 94:156735v (1980).

*Primary Examiner*—Jeffrey E. Russel
*Attorney, Agent, or Firm*—Paul R. Darkes; Martin F. Savitzky

[57] ABSTRACT

This invention relates to N-arylcarbamoyl proline analogues which are useful as cholecystokinin and gastrin antagonists, to pharmaceutical compositions including such proline analogues, and to their use in preventing or treating cholecystokinin or gastrin related disorders.

19 Claims, No Drawings

COMPOUNDS HAVING CHOLECYSTOKININ AND GASTRIN ANTAGONISTIC PROPERTIES

BACKGROUND OF THE INVENTION

1. Field of the Invention

This invention relates to certain compounds which antagonize the actions of the neuropeptides cholecystokinin (hereinafter CCK) and gastrin.

CCK and gastrin are peptides, endogenous in human and other species, which regulate biological functions in tissues in the GI tract and central nervous system (CNS). Gastrin and CCK regulate biological activity by acting as autocrine, parocrine, endocrine or neurocrine agents.

The first and principal form of gastrin isolated was the 17 amino acid residue peptide, G-17 or little gastrin. The second major molecular form of gastrin is the 34 amino acid residue peptide, G-34 or big gastrin. G-34 is considered the proform of G-17, but both forms of gastrin are biologically active and nearly equipotent. The smallest residue possessing full biological activity is G-4 which is the final 4 amino acids at the carboxy terminal. Sulfation of the tyrosine residue (6-amino acids from the C-terminal) is not necessary for expression of the bioactivity of gastrin and its congeners.

The major physiologic action of gastrin is the stimulation of acid secretion from the stomach. Gastrin stimulates acid secretion by at least three separate actions: direct stimulation of parietal cell activity; potentiating the actions of histamine, a paracrine stimulus; and by direct release of histamine.

Gastrin is a trophic hormone for gastric, fundic and intestinal mucosa and for the pancreas. Gastrin directly stimulates those biochemical processes, DNA and RNA synthesis, that are involved in tissue growth.

Gastrin also stimulates pepsin secretion and increases gastric mucosal blood flow. It causes electrolyte and water secretion by the stomach, pancreas, liver, and Brunner's glands.

Other possible actions of gastrin may involve the regulation of lower esophageal sphincter contraction and other smooth muscle contractions (motility) in the GI tract.

CCK is a linear amino acid polypeptide that occurs in several bioactive molecular forms: CCK-8, CCK-22, CCK-33, CCK-39 and CCK-58 are the major forms which have been reported. All of the CCK variants require the sulfation of the tyrosine residue at position 7, counting from the C-terminal, for the full expression of their biologic activity.

The principal physiclogic actions of CCK are stimulation of gallbladder contraction and of pancreatic enzyme secretion. There is evidence which supports a physiclogic role of CCK in the inhibition of gastric emptying, stimulation of pancreatic growth and release of pancreatic polypeptide.

Other possible actions of CCK include stimulation of insulin, glucagon, somatostatin and peptide YY release, stimulation of hepatic bile flow, intestinal motility, blood flow in the superior mesenteric artery, secretion of pepsinogen from gastric glands, and secretion of bicarbonate from the stomach and duodenum. In contrast to gastrin, CCK relaxes the lower esophageal sphincter.

In the nervous system CCK may act as a neurotransmitter or as a neuromodulator. As such, exogenous CCK has been shown to affect memory. Also levels of acetylcholine and dopamine have been affected by exogenous CCK. CCK has been implicated as well for producing the satiety effect, however, it is not clear if this is regulated by peripheral or central mechanisms.

There is considerable overlap in the biological activities elicited by gastrin and CCK. Therefore, gastrin receptor antagonists may also possess activity at the CCK receptors or vice versa.

2. Reported Developments

Four distinct chemical classes of CCK-A (peripheral CCK) receptor antagonists have been reported (see R. M. Freidinger, Medicinal Research Reviews, 9(3), 271–290 (1989)).

(1) Cyclic nucleotides, e.g. dibutyryl cyclic GMP (see N. Boilos et al., Am. J. Physiol. 242, G 161 (1982) and P. Robberecht et al., Mol. Pharmacol., 17, 268 (1982)).

(2) Amino acid derivatives, characterized by proglumide, a derivative of glutamic acid and N-acylated tryptophans, i.e. para-chlorobenzoyl-L-tryptophan (benzotript) (see W. F. Hahne et al., Proc. Natl. Acad. Sci. USA, 78: 6304 (1981) and R. T. Jensen et al., Biochem. Biophys. Acta. 76, 269 (1983)); also second generation proglumide analogues typified by Lorglumide and Loxiglumide (F. Makovec et al., Arzneim-Forsch., 37(II), 1265 (1987)). The latter two analogues have considerably better receptor affinity and selectivity.

(3) Peptide and pseudopeptide analogs based on the C-terminal end of CCK, especially analogues of CCK-8, cholecystokinin tyrosine-sulfated octapeptide Some examples are cholecystokinin-27-32-amide (M. Spanarkel et al., J. Biol. Chem. 258, 6746 (1983)) and a synthetic peptide derivative of cholecystokinin containing D-tryptophan and norleucine (M. F. Lignon et al. J. Biol. Chem. 262, 7226 (1987)).

(4) Non-peptide structures, e.g. the fermentation product asperlicin (R. S. L. Chang et al., Science 230, 177 (1985)). Subsequent medicinal chemistry done on this compound culminated in the 1,4-benzodiazepine (MK329) series having very high CCK-A affinity (B. E. Evans et al., J. Med. Chem. 31, 2235–2246 (1988)).

Structurally related compounds which retain nanomolar level potency for the CCK-A receptor have recently been reported, e.g. 3-aminobenzolactam (R. S. L. Chang and W. H. Parsons, Eur. Pat. Appl. EP 166,345 (1986), and W. H. Parsons et al., J. Med. Chem., 32, 1681–1685 (1989) and β-carbolines (B. E. Evans, Eur. Pat. Appl. EP 304,233 (1988) and M. Itonaga et al., Japan. J. Pharmacol., 46, 319–324 (1988)).

Compounds selective for the peripheral gastrin receptor also possess strong affinity for the CCK-B receptor (a CCK receptor located in the CNS). Presently there are no known agents which differentiate substantially between the CCK-B receptor and the peripheral gastrin receptor. Compounds selective for gastrin generally fall into two major classes.

(1) Peptide and pseudopeptide analogs based on C-terminal amino acids of CCK or gastrin, especially CCK-4 (the C-terminal tetrapeptide of gastrin). Some examples are the pseudopeptide in which the peptide bond between leucine and aspartic acid of Boc-CCK-4 has been replaced by CH$_2$NH bond and has the same binding affinity as Boc-CCK-4 but has no agonist activity (J. Martinez et al., J. Med. Chem., 28, 1874, (1985)).

Other analogues of CCK-4 containing partial retro-inverso modifications have been demonstrated to bind strongly to the gastrin receptor and block the effects of gastrin in the rat (in vivo) (M. Rodriguez et al., *J. Med. Chem.*, 30, 758–763, (1987)).

Recently some cyclic cholecystokinin analogues of CCK-8 have demonstrated selectivity for the CCK-B (CNS) receptor relative to CCK-A (peripheral ), B. Charpentier, et al., *Proc. Natl. Acad. Sci. USA*, 85, 1968–1972, (1988).

(2) Benzodiazepines. The 3-substituted 1,4-benzodiazepines effective as selective antagonists of CCK-A have been modified synthetically resulting in agents selective for the peripheral gastrin and CCK-B (brain) receptors, such as the Merck compound L-365,260 (V. J. Lotti and R. S. L. Chang, *Eur. J. of Pharm.*, 162, 273–280 (1989), also M. G. Bock et al., *J. Med. Chem.*, 32, 16–23, (1989)).

Other non-peptide, non-benzodiazepine compounds (e.g. analogs of Virginiamycin M1) have been reported to display strong binding affinity and selectively for gastrin (relative to CCK-A) (Y.-K. T. Lam et al., U.S. Pat. No. 4,762,923 (1988)).

Tetrahydropyridoindoles are reported to be active as gastrin and cholecystokinin antagonists in pending U.S. application Ser. No. 07/542,495, attorney docket no. A0135, filed on Jun. 21, 1990, now abandoned, and U.S. application Ser. No.: 07/573,514, attorney Docket No.: A0135A, filed Aug. 24, 1990, now U.S. Pat. No. 5,162,336, assigned to the same assignee as the present invention.

The present invention relates to novel N-arylcarbamoyl proline analogues which are useful as cholecystokinin and gastrin antagonists.

SUMMARY OF THE INVENTION

Compounds of the present invention are described by Formula I

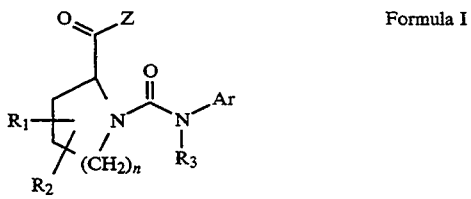

Formula I wherein

Ar is aryl;

$R_1$ and $R_2$ are independently hydrogen, alkyl, aryl, aralkyl, hydroxy, alkoxy, aryloxy, aralkoxy, halo, —$NR_4R_5$ where $R_4$ and $R_5$ are independently hydrogen, alkyl, aralkyl, or aryl, or when $R_1$ and $R_2$ are vicinal, $R_1$ and $R_2$, together with the carbon atoms to which they are attached, may form an unsubstituted or substituted carbocyclic ring containing from about four to about seven carbon atoms in the ring, which is fused to the nitrogen-containing ring of Formula I;

$R_3$ is hydrogen or alkyl;

Z is unsubstituted or substituted nitrogen-containing heterocyclyl, —$NR_aR_b$ where $R_a$ and $R_b$ are independently hydrogen, alkyl, aryl, aralkyl, or when taken together, $R_a$ and $R_b$ may form —$(CH_2)_t$— where t is 3, 4, or 5, or Z is a mono-, di- or tripeptidyl group or analogue or derivative thereof; and n is 0, 1, 2, or 3;

or pharmaceutically acceptable salts thereof.

Additionally, this invention relates to to pharmaceutical compositions including such compounds, and to their use in preventing or treating cholecystokinin or gastrin related disorders.

DETAILED DESCRIPTION OF THE INVENTION

As used above, and throughout the description of this invention, the following terms, unless otherwise indicated, shall be understood to have the following meanings:

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain. Preferred alkyl groups are the "lower alkyl" groups which are those alkyl groups having from 1 to about 6 carbons.

"Aryl" means phenyl or naphthyl or phenyl or naphthyl substituted with one or more aryl group substituents which may be the same or different, where "aryl group substituent" includes alkyl, alkenyl, alkynyl, aryl, aralkyl, hydroxy, alkoxy, aryloxy, aralkoxy, hydroxyalkyl, acyl, formyl, carboxy, alkenoyl, aroyl, halo, nitro, trihalomethyl, cyano, alkoxycarbonyl, aryloxycarbonyl, aralkoxycarbonyl, acylamino, aroylamino, carbamoyl, alkylcarbamoyl, dialkylcarbamoyl, arylcarbamoyl, aralkylcarbamoyl, alkylsulfonyl, alkylsulfinyl, arylsulfonyl, arylsulfinyl, aralkylsulfonyl, aralkylsulfinyl, or —NRR' where R and R' are independently hydrogen, alkyl, aryl, or aralkyl.

"Carbocyclic ring" means a non-aromatic or aromatic ring composed of carbon atoms. Preferred carbocyclic rings include cyclopentyl, cyclohexyl, cycloheptyl, and phenyl.

"Substituted carbocyclic ring" means a carbocyclic ring substituted with one or more substituents, which may be the same or different, including, where the carbocyclic ring is non-aromatic, alkyl, aryl, aralkyl, hydroxy, alkoxy, aryloxy, aralkoxy, or halo, and where the carbocyclic ring is aromatic, aryl group substituents.

"Analogue" means a compound which comprises a chemically modified form of a specific compound or class thereof, and which maintains the pharmaceutical and/or pharmacological activities characteristic of said compound or class.

"Derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

"Peptidyl group" means a synthetic or naturally occurring amino acid group. Preferred peptidyl groups include glycyl, alanyl, valyl, leucyl, isoleucyl, seryl, threonyl, phenylalanyl, tyrosyl, tryptophanyl, cysteyl, methionyl, prolyl, hydroxyprolyl, aspartyl, asparginyl, glutamyl, glutaminyl, histidyl, arginyl, and lysyl.

"Aralkyl" means an alkyl group substituted by an aryl radical. Exemplary aralkyl groups include benzyl and phenethyl.

"Alkoxy" means an alkyl-O— group. Lower alkoxy groups are preferred. Exemplary groups include methoxy, ethoxy, n-propoxy, i-propoxy and n-butoxy.

"Aryloxy" means an aryl-O— group. Exemplary groups include phenoxy and 2-naphthyloxy.

"Aralkoxy" means an aralkyl-O— group. Exemplary groups include benzyloxy and phenethyloxy.

"Alkylene" means a straight or branched bivalent hydrocarbon chain having from 1 to about 20 carbon atoms. The preferred alkylene groups are the lower alkylene groups having from 1 to about 6 carbon atoms. Exemplary groups include methylene and ethylene.

"Phenylene" means a 1,2-, 1,3- or 1,4- bivalent phenyl group which may be unsubstituted or substituted with one or more aryl group substituents.

"Cycloalkylene" means a bivalent, saturated carbocyclic group having about 4 to about 8 carbon atoms. Preferred cycloalkylene groups include 1,2-, 1,3-, or 1,4- cis or trans-cyclohexanylene.

"Aralkylalkylene" means an alkylene group substituted with an aryl group.

"Alkylalkylene" means an alkylene group substituted with an alkyl group. Preferred groups include methylmethylene and i-propylmethylene.

"Alkenyl" means an alkyl group containing a carbon-carbon double bond. Exemplary groups include allyl and vinyl.

"Alkynyl" means an alkyl group containing a carbon-carbon triple bond. Exemplary groups include ethynyl and propargyl.

"Acyl" means an

group. Preferred acyl groups are those in which the alkyl group is lower alkyl.

"Aroyl" means an

group. Exemplary groups include benzoyl and 1- and 2-naphthoyl.

"Alkenoyl" means an

group.

"Alkoxycarbonyl" means an

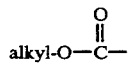

group. Preferred groups include methoxycarbonyl and ethoxycarbonyl.

"Aralkoxycarbonyl" means an

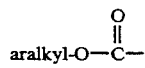

group, A preferred group is benzyloxycarbonyl.

"Aryloxycarbonyl" means an

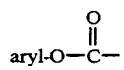

group. A preferred group is phenoxycarbonyl.

"Carbamoyl" is an

group.

"Alkylcarbamoyl" is an

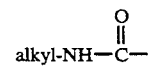

group.

"Dialkyl carbamoyl" is an

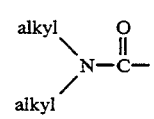

group where the alkyl groups may be the same or different.

"Acylamino" is an acyl-NH- group.

"Aroylamino" is an aroyl-NH- group.

"Halo" means fluoro, chloro, bromo, or iodo.

"Hydroxyalkyl" means an HO-alkyl- group. Preferred groups include hydroxymethyl and hydroxyethyl.

"Aralkylsulfonyl" means an

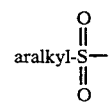

group.

"Aralkylsulfinyl" means an

group.

"Alkylsulfonyl" means an

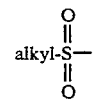

group. Preferred groups are those in which the alkyl group is lower alkyl.

"Alkylsulfinyl" means an

group. Preferred groups are those in which the alkyl group is lower alkyl.

"Arylsulfonyl" means an

group.

"Arylsulfinyl" means an

group.

"Substituted phenyl" means a phenyl group substituted by one or more aryl group substituents.

"Substituted naphthyl" means a 1- or 2-naphthyl group substituted by one or more aryl group substituents.

"Nitrogen-containing heterocyclyl" means about a 4- to about a 15-membered monocyclic or multicyclic ring system in which one or more of the atoms in the ring or rings is an element other than carbon, for example nitrogen, oxygen or sulfur, which contains at least one basic nitrogen atom in the ring or rings, and which is attached by that basic nitrogen atom. Preferred nitrogen-containing heterocyclyl groups include 2,3-dihydro-1H-pyrrol[3,4b]quinolin-2-yl, 1,2,3,4-tetrahydrobenz [b][1,7]naphthyridin-2-yl, 1,2,3,4-tetrahydrobenzo[b][1,6]naphthyridin-2-yl, 1,2,3,4-tetrahydro-9H-pyrido[3,4b]indol-2-yl, 1,2,3,4-tetrahydro-9H-pyrido[4,3-b]indol-2-yl, 2,3,-dihydro-1H-pyrrolo[3,4-b]indol-2-yl, 1H-2,3-dihydroisoindol-2-yl, 2,3-dihydrobenz[f]isoquinolin-2-yl, 1,2,3,4-tetrahydrobenz[g]isoindol-2-yl, 1H-2,3,4,5-tetrahydroazepino[3,4-b]indol-2-yl, 1H-2,3,4,5-tetrahydroazepino[4,3b]indol-3-yl, and 1H-2,3,4,5-tetrahydroazepino[4,5-b]indol-2-yl.

"Substituted nitrogen-containing heterocyclyl" means a nitrogen-containing heterocyclyl substituted by one or more aryl group substituents.

"Carboxyalkylalkylene" means an

group. Preferred groups include carboxymethylmethylene and carboxyethylmethylene.

"Alkoxycarbonylalkylalkylene" means an

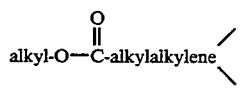

group. Preferred groups include methoxy- and ethoxycarbonylmethyl- and carbonylethyl- methylene.

"Aryloxycarbonylalkylalkylene" means an

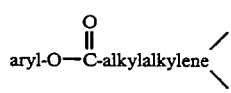

group. Preferred groups include phenoxycarbonylmethyl- and phenoxycarbonylethyl- methylene.

"Aralkoxycarbonylalkylalkylene" means an

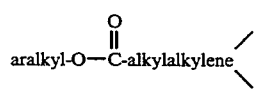

group. Preferred groups include benzyloxycarbonylmethyl- and benzyloxycarbonylethyl- methylene.

"Carbamoylakylalkylene" means an

group. Preferred groups include carbamoylmethyl- and carbamoylethyl- methylene.

"Alkylthioalkylalkylene" means an

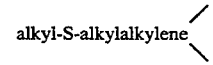

group. A preferred group is methylthioethylmethylene.

"Guanidinoalkylalkylene" means an

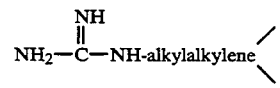

group. Preferred groups include guanidinopropyl- and guanidinobutylmethylene.

"Aminoalkylalkylene" means an

group. Preferred groups include aminopropyl- and aminobutyl- methylene.

"Carboxyalkyl" means an HOOC-alkyl- group. Preferred groups include carboxymethyl and carboxyethyl.

"Alkoxycarbonylalkyl" means an

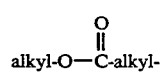

group. Preferred groups include methoxy- and ethoxycarbonylmethyl and carbonyl ethyl.

"Aryloxycarbonylalkyl" means an

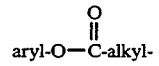

group. Preferred groups include phenoxycarbonylmethyl and ethyl.

"Aralkoxycarbonylalkyl" means an

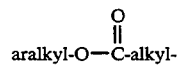

group. Preferred groups include benzyloxy- methyl and ethyl.

A preferred class of compounds of the present invention is described by Formula I wherein:

$R_1$ and $R_2$ are independently hydrogen, alkyl, aryl, aralkyl, hydroxy, alkoxy, aryloxy, aralkoxy, halo, —$NR_4R_5$, or, when $R_1$ and $R_2$ are vicinal, $R_1$ and $R_2$ may be taken together to be

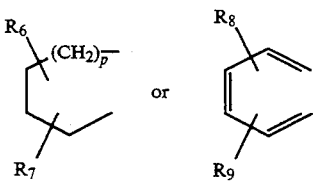 or 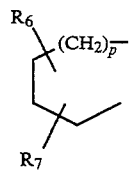

where $R_6$ and $R_7$ are independently hydrogen, alkyl, aryl, aralkyl, hydroxy, alkoxy, aryloxy, aralkoxy, or halo, and $R_8$ and $R_9$ are independently hydrogen, or an aryl group substituent, and p is 0, 1, or 2; and Z is unsubstituted or substituted nitrogen-containing heterocyclyl, —NR$_a$R$_b$,

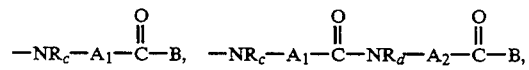

where

A$_1$ and A$_2$ are independently alkylene, phenylene, cycloalkylene, arylalkylene, arylalkylalkylene, alkoxycarbonylalkylalkylene, aryloxycarbonylalkylalkylene, aralkoxycarbonylalkylalkylene, carboxyalkylalkylene, carbamoylalkylalkylene, alkylthioalkylalkylene, hydroxymethylmethylene, (1-hydroxyethyl)methylene, (4-hydroxyphenyl)methylmethylene, indol-3-ylmethylmethylene, imidazol-4-ylmethylmethylene, guanidinoalkylalkylene, or aminoalkylalkylene, B is hydroxy, alkoxy, aralkoxy, aryloxy or —NR$_f$R$_g$ where R$_f$ and R$_g$ are independently hydrogen, alkyl, aralkyl, carboxyalkyl, alkoxycarbonylalkyl, aryloxycarbonylalkyl or aralkoxycarbonylalkyl, R$_c$ and R$_d$ are independently hydrogen, alkyl, aryl, or aralkyl;

—NR$_c$-A$_1$- may be

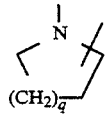

where q is 0, 1, 2, or 3; and
—NR$_d$-A$_2$- may be

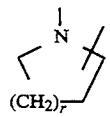

where r is 0, 1, 2, or 3.

Another preferred class of compounds of the present invention is described by Formula I wherein R$_1$ and R$_2$ are vicinal and are taken together to be Still another preferred class of compounds of the present invention is described by Formula I wherein R$_1$ and R$_2$ are vicinal and are taken together to be

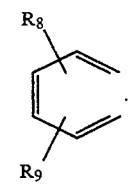

A more preferred class of compounds of the present invention is described by Formula I wherein Z is unsubstituted or substituted nitrogencontaining heterocyclyl.

Another more preferred class of compounds of the present invention is described by Formula I wherein R$_1$ and R$_2$ are independently hydrogen, alkyl, aryl, aralkyl, hydroxy, alkoxy, aryloxy, aralkoxy, halo, or NR$_4$R$_5$.

A most preferred class of compounds of the present invention is described by Formula I wherein Z is

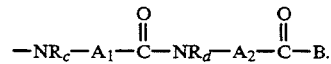

A special embodiment of the present invention is described by Formula II below.

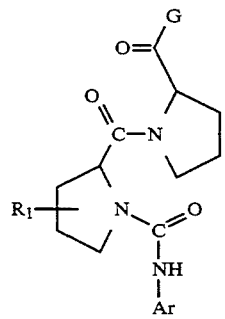

Formula II wherein
R$_1$ is substituted or unsubstituted aralkoxy; and
G is

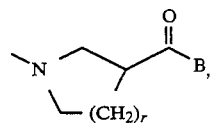

-continued

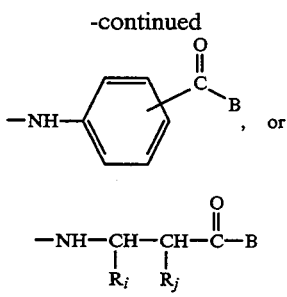

, or $$-NH-CH-CH-\overset{O}{\overset{\|}{C}}-B$$
$$\phantom{-NH-}R_i \phantom{-CH-}R_j$$

where
B is hydroxy, alkoxy, aralkoxy, aryloxy or -NR$_f$R$_g$ where R$_f$ and R$_g$ are independently hydrogen, alkyl, or aralkyl; and R$_i$ and R$_j$ are independently hydrogen, alkyl, or R$_i$ and R$_j$ may be taken together to be -(CH$_2$)$_u$- where u is 2, 3, 4, or 5.

Representative compounds of the present invention include:

2-[(N-(3-methyl)phenylcarbamoyl-4(R)-benzyloxy)-L-prolyl]- 1,2,3,4-tetrahydro-9H-pyrido[3,4-b]indole, 2-[(N-(4-methoxy)phenylcarbamoyl-4(R)-benzyloxy)-L-prolyl]- 1,2,3,4-tetrahydro-9 H-pyrido[3,4-b]indole, 2-[(N-(3-methyl)phenylcarbamoylindolin-2 (S)-yl)carbonyl]- 1,2,3,4-tetrahydro-9 H-pyrido[3,4-b]indole, 2-(N-naphth-2-ylcarbamoyl-D-prolyl)- 1,2,3,4-tetrahydro-9H-pyrido[3,4b]indole, 2-[N-(3-methyl)phenylcarbamoyl-D-prolyl]- 1,2,3,4-tetrahydro-9H-pyrido[3,4-b]indole, 2-[N-(3-methyl)phenylcarbamoyl-L-prolyl]- 1,2,3,4-tetrahydro-9H-pyrido[3,4-b]indole, N-[4(R)-benzyloxy-N-(3-methyl)phenylcarbamoyl)-L-prolyl]-D-leucyl-D-aspartic acid amide, 2-[(N-(4(R)-hydroxy-N-(3,4-dichloro)phenylcarbamoyl-D-prolyl)-L-prolyl)amino]benzoic acid, 2-[(N-(4(R)-benzyloxy-N-naphth-2-ylcarbamoyl-L-prolyl)-L-prolyl)amino]benzoic acid, 2-[(N-(4(R)-benzyloxy-N-(3,4-dichloro)phenylcarbamoyl-L-prolyl)-L-prolyl)amino]benzoic acid, 2-[(N-(4(R)benzyloxy-N-naphth-2-ylcarbamoyl-L-prolyl)-L-prolyl)amino]benzoic acid, 2-[(N-(4(R)benzyloxy-N-naphth-1 -ylcarbamoyl-L-prolyl)-L-prolyl)amino]benzoic acid, and 3-[(N-(4(R)benzyloxy-N-(3,4-dichloro)phenylcarbamoyl-D-prolyl)-L-prolyl)amino]propanoic acid.

The compounds of the present invention contain asymmetric centers. These asymmetric centers may independently be in either the R or S configuration. The present invention comprises the individual stereoisomers and mixtures thereof.

The compounds of the present invention may be useful in the form of the free base or acid or in the form of a pharmaceutically acceptable salt thereof. All forms are within the scope of the invention.

Where the compound of the present invention is substituted with a basic moiety, acid addition salts may be formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial gastrin and cholecystokinin antagonist properties inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are nontoxic to the animal organism in pharmaceutical doses of the salts, so that the beneficial gastrin and cholecystokinin antagonistic properties inherent in the free acid are not vitiated by side effects ascribable to the cations. Pharmaceutically acceptable salts within the scope of the invention are those derived from the following bases: sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydroxide, carbonate or similar reactive compound of the chosen metal in an aqueous solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

Compounds of this invention may be prepared in accordance with the reaction sequences described below, or can be prepared by methods known in the art. The starting materials used in the preparation of compounds of this invention are known or are commercially available, or can be prepared by known methods or by specific reaction schemes described herein.

The compounds of the present invention are available, generally, by coupling the carboxyl group of a proline analogue to an appropriate amine, nitrogen-containing heterocycle, amino acid, or peptide derivative followed by reaction of the resulting proline analogue derivative with an aryl isocyanate or an N-aryl-N-alkyl carbamoyl chloride to give the N-arylcarbamoyl proline analogue derivative. If necessary or desirable, this order of addition may be reversed.

If it is necessary or desirable to prevent cross-reaction between chemically active substituents, either on the proline analogue or on compounds to be reacted with the proline analogue, the substituents may be protected by standard blocking groups which may subsequently be removed or retained, as required, by known methods to afford the desired product (see, for example, Green, "Protective Groups in Organic Synthesis", Wiley, New York, 2981). Selective protection or deprotection may also be necessary or desirable to allow conversion or removal of existing substituents, or to allow subsequent reaction to afford the final desired product.

The general method of preparation of compounds of the present invention is shown in Scheme I below.

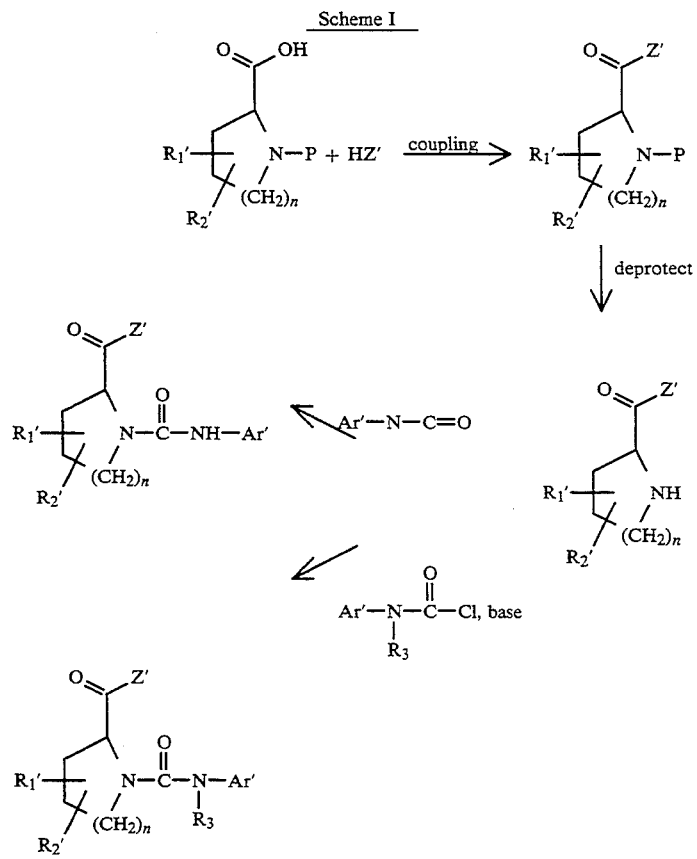

Where $R_1'$, $R_2'$, $Z'$, and $Ar'$ represent $R_1$, $R_2$, $Z$, and $Ar$ as defined above, respectively, or represent protected derivatives thereof, or precursor moieties thereto, and P represents an amino-protecting group.

The amino-protected proline analogue is coupled with the appropriate amine derivative, by methods known in the art, to form the amide. Preferred methods are: treatment of the mixed anhydride, formed by treatment of the carboxylic acid with isopropyl chloroformate in the presence of an organic base such as triethylamine or N-methyl piperidine, with the amine in an aprotic organic solvent-such as tetrahydrofuran or methylene chloride; treatment of the carboxylic acid with bis(2-oxo-3-oxazolidinyl)phosphinic chloride in an aprotic solvent such as tetrahydrofuran in the presence of triethylamine, followed by reaction with the amine; and treatment of the carboxylic acid with isopropenyl chloroformate in an aprotic solvent such as methylene chloride in the presence of N-methyl morpholine followed by reaction with the amine in the presence of 4-dimethylaminopyridine. A preferred amino-protecting group is the tertbutoxycarbonyl group.

Deprotection, i.e. removal of the amino-protecting group, is accomplished by known methods to afford the free amine form of the proline analogue. A preferred method of deprotection is that of treating the tertbutoxycarbonyl derivative with trifluoroacetic acid in methylene chloride.

The resulting free amine form of the proline analogue is then treated with an aryl isocyanate in an aprotic solvent such as tetrahydrofuran or methylene chloride, or with an N-alkyl aryl carbamoyl chloride in an aprotic solvent in the presence of an organic base such as triethylamine to give the compounds of the present invention, protected derivatives thereof, or derivatives thereof containing precursor moieties thereto. The protected derivatives may then be deprotected by known methods or the derivatives containing precursor moieties may be further treated by known methods to afford the compounds of the present invention.

As noted above, compounds of the present invention have asymmetric carbon atoms which may, individually, be in either the R or S configuration. As a result, the compounds may be obtained as individual enantiomers, racemic mixtures, or, when two or more asymmetric carbon atoms are present, as a mixture of diastereomers. The product may be synthesized as a mixture of isomers and then the desired isomer separated by conventional techniques such as chromatography or fractional crystallization in the case where diastereomers are to be separated, or by chiral chromatography or separation of diastereomeric salts or derivatives of the isomers by fractional crystallization or chromatography in the case enantiomers, followed by reisolation of the desired product by conventional techniques. Alternatively, synthesis of the compounds may be carried by known stereospecific processes, or by using the appropriate form of intermediates which would result in obtaining the desired stereoisomer.

The present invention is further explained by the following illustrative examples.

EXAMPLE 1

Preparation of
2-[(N-(3-methyl)phenylcarbamoyl-4(R)-benzyloxy)-L-prolyl]1,2,3,4-tetrahydro-9H-pyrido[3,4-b]indole Step 1: Preparation of
2-[(N-tert-butoxycarbonyl-4(R)-benzyloxy)-L-prolyl]1,2,3,4-tetrahydro-9H-pyrido[3,4-b]indole A solution of N-α-tert-butoxycarbonyl-O-benzyl-L-4-hydroxyproline (0.5 g) in tetrahydrofuran (16 ml)is cooled to −20° C., triethylamine (0.19 g) and bis(2-oxo-3-oxazolidinyl)phosphinic chloride (0.48 g) are added and the solution stirred at −20° C. for about 40 minutes. The solution is concentrated in vacuo at room temperature to approximately one-half of its original volume and cooled to 0° C. To this solution is added a solution of 1,2,3,4-tetrahydro-9H-pyrido[3,4-b]indole (0.27 g) and triethylamine (0.19 g) in dimethylformamide (hereinafter DMF) (8 ml). The resulting solution is stirred at 0° C. for about 3 hours, then at room temperature overnight and concentrated in vacuo. The residue is dissolved in ethyl acetate and the solution washed with 1N hydrochloric acid, saturated sodium bicarbonate solution and brine. The organic solution is dried over magnesium sulfate, filtered, and concentrated in vacuo. The crude product is purified by flash chromatography eluting with 10% acetone in methylene chloride to give the desired product. Step 2: Preparation of 2-(4(R)-benzyloxy-L-prolyl)-1,2,3,4-tetrahydro-9H-pyrido[3,4-b]indole A solution of 2-[(N-tert-butoxycarbonyl-4(R)-benzyloxy)-L-prolyl]-1,2,3,4-tetrahydro-9H-pyrido[3,4-b]indole (0.50 g) in methylene chloride (5 ml) is cooled to 0° C. Trifluoroacetic acid (2.4 g) is added dropwise and the solution is stirred at 0° C. for about 4 hours. The solution is concentrated in vacuo and two portions of toluene (10 ml) are evaporated from the residue to give the desired product as the trifluoroacetate salt which is used, without further treatment, for the next step.

Step 3: Preparation of
2-[(N-(3-methyl)phenylcarbamoyl-4(R)-benzyloxy)-L-prolyl]-1,2,3,4-tetrahydro-9H-pyrido[3,4-b]indole To a solution of the trifluoroacetate salt of 2-(4(R)-benzyloxy-L-prolyl)1,2,3,4-tetrahydro-9H-pyrido[3,4-b]indole (0.26 g) in methylene chloride (5 ml) is added triethylamine (0.064 g). The solution is stirred for about 5 minutes and m-tolyl isocyanate (0.07 g) is added, the solution stirred at room temperature overnight, then diluted with ethyl acetate (75 ml). The solution is washed with 10% hydrochloric acid, saturated sodium bicarbonate and brine. The organic solution is dried over sodium sulfate, filtered and concentrated in vacuo. The crude product is purified by flash chromatography eluting with a gradient of 15% to 33% ethyl acetate in methylene chloride to give the desired product, m.p. 113°–115° C.

EXAMPLE 2

Preparation of
2-[(N-(4-methoxy)phenylcarbamoyl-4(R)-benzyloxy)-L-prolyl]-1,2,3,4-tetrahydro-9H-pyrido[3,4-b]indole Using essentially the procedure of Example 1, Step 3, the desired product, m.p. 96°–100° C., is prepared from 4-methoxyphenylisocyanate.

EXAMPLE 3

Preparation of
2-[(N-(3-methyl)phenylcarbamoylindolin-2(S)-yl)carbonyl]-1,2,3,4-tetrahydro-9H-pyrido[3,4-b]indole Step 1: Preparation of
(S)-N-tert-butoxycarbonylindoline-2-carboxylic acid To a solution of (S)-indoline-2-carboxylic acid (1.0 g) in 1N aqueous sodium hydroxide (12 ml) is added a solution of di-tert-butyl dicarbonate (1.47 g) in tert-butanol (9 ml) and the solution is stirred at room temperature for about 2 days. The aqueous solution is adjusted to pH 2 with 1N hydrochloric acid, extracted with ethyl acetate and the ethyl acetate solution dried over magnesium sulfate, filtered and concentrated in vacuo to give the desired product which is used, without further treatment, for the next step.

Step 2: Preparation of
2-[(N-tert-butoxycarbonylindolin-2(S)-yl)carbonyl]-1,2,3,4-tetrahydro-9H-pyrido[3,4-b]indole Using essentially the procedure of Example 1, Step 1, and purifying the crude product using flash chromatography in a gradient of 20% to 40% ethyl acetate in hexane, the desired product is prepared from (S)-N-tert-butoxycarbonylindoline-2-carboxylic acid.

Step 3: Preparation of
2-[(Indolin-2(S)-yl)carbonyl]-1,2,3,4-tetrahydro-9H-pyrido[3,4-b]indole Using essentially the procedure of Example 1, Step 2, the desired product is prepared, as the trifluoroacetate salt, from 2-[(N-tertbutoxycarbonylindolin-2(S)-yl)carbonyl]-1,2,3,4-tetrahydro-9H-pyrido[3,4b]indole.

Step 4: Preparation of 2-[(N-(3-methyl)phenylcarbamoylindolin-2(S)-yl)carbonyl]-1,2,3,4-tetrahydro-9H-pyrido[3,4-b]indole Using essentially the procedure of Example 1, Step 3, the desired product, m.p. 146° C. (dec.), is prepared from the trifluoroacetate salt of 2[(Indolin-2(S)-yl)carbonyl]-1,2,3,4-tetrahydro-9H-pyrido[3,4-b]indole.

EXAMPLE 4

Preparation of 2-(N-naphth-2-ylcarbamoyl-D-prolyl)-1,2,3,4-tetrahydro-9H-pyrido[3,4-b]indole

Step 1: Preparation of 2-(N-tert-butoxycarbonyl-D-prolyl)-1,2,3,4-tetrahydro-9H-pyrido[3,4-b]indole Using essentially the procedure of Example 1, Step 1, the desired product is prepared from N-tert-butoxycarbonyl-D-proline.

Step 2: Preparation of 2-D-prolyl-1,2,3,4-tetrahydro-9H-pyrido[3,4-b]indole

Using essentially the procedure of Example 1, Step 2, the desired product is prepared, as the trifluoroacetic salt, from 2-(N-tert-butoxycarbonyl-D-prolyl)-1,2,3,4-tetrahydro-9H-pyrido[3,4-b]indole.

Step 3: Preparation of 2-(N-naphth-2-ylcarbamoyl-D-prolyl)-1,2,3,4-tetrahydro-9H-pyrido[3,4-b]indole Using essentially the same procedure of Example 1, Step 3, and purifying the crude product by flash chromatography eluting with a gradient of 10% to 20% acetone in methylene chloride, the desired product, m.p. 152°–155° C. is prepared from the trifluoroacetate salt of 2-D-prolyl-1,2,3,4-tetrahydro-H-pyrido[3,4-b]indole and 2-naphthyl isocyanate.

EXAMPLE 5

Preparation of 2-[N-(3-methyl)phenylcarbamoyl-D-prolyl]-1,2,3,4-tetrahydro-9H-pyrido[3,4-b]indole Using essentially the procedure of Example 4, the desired product is prepared as the hemihydrate, m.p. 112°–115° C.

EXAMPLE 6

Preparation of 2-[N-(3-methyl)phenylcarbamoyl-L-prolyl]-1,2,3,4-tetrahydro-9H-pyrido[3,4-b]indole Using essentially the procedure of Example 4, the desired product, m.p. 114°–116° C. is prepared.

EXAMPLE 7

Preparation of N-[4(R)-benzyloxy-N-(3-methyl)phenylcarbamoyl)-L-prolyl]-D-leucyl-D-aspartic acid amide

Step 1: Preparation of N(N-α-tert-butoxycarbonyl-O-benzyl-L-hydroxyprolyl)-D-leucyl-D-aspartic acid amide benzyl ester To a solution of N-α-tert-butoxycarbonyl-O-benzyl-L-4-hydroxyproline (0.5 g) in methylene chloride (4 ml)is added N-methylpiperidine (0.19 ml) and a solution of isopropyl chloroformate (1.0 M in toluene, 1.4 ml). After stirring the solution at 0° C. for about 2 minutes, a solution of D-leucyl-D-aspartic acid amide benzyl ester trifluoroacetate salt (1.4 mmol) and N-methylpiperidine (0.31 g) in methylene chloride (4 ml) is added and the solution stirred at 0° C. for about 2 hours, then at room temperature overnight. The solution is diluted with ethyl acetate and the organic layer washed with water, 1N hydrochloric acid, 10% sodium carbonate solution, then dried over magnesium sulfate, filtered and concentrated in vacuo. The crude product is triturated in ether/hexane (1:1) to give the desired product.

Step 2: Preparation of N-(O-benzyl-L-hydroxyprolyl)-D-leucyl-D-aspartic acid amide benzyl ester Using essentially the procedure of Example 1, Step 2, the desired product is prepared, as the trifluoroacetate salt, from N(N-α-tert-butoxycarbonyl-O-benzyl-L-hydroxyprolyl)-D-leucyl-D-aspartic acid amide benzyl ester.

Step 3: Preparation of N-[(N-(3-methyl)phenylcarbamoyl-4(R)-benzyloxy)-L-prolyl]-D-leucyl-D-aspartic acid amide benzyl ester Using essentially the procedure of Example 1, Step 3, and purifying the crude product by flash chromatography eluting with a gradient of 80% to 100% ethyl acetate in methylene, the desired product is prepared from the trifluoroacetate salt of N(O-benzyl-L-hydroxyprolyl)-D-leucyl-D-aspartic acid amide benzyl ester.

Step 4: Preparation of N-[4(R)-benzyloxy-N-(3-methyl)phenylcarbamoyl)-L-prolyl]-D-leucyl-D-aspartic acid amide To a solution of N-[(N-(3-methyl)phenylcarbamoyl-4(R)-benzyloxy)-L-prolyl]-D-leucyl-D-aspartic acid amide benzyl ester (0.38 g) in tetrahydrofuran (6 ml) is added 10% palladium on carbon (0.08 g) and the mixture stirred under hydrogen at atmospheric pressure for about 6 hours. The mixture is filtered and concentrated in vacuo to give the desired product, m.p. 65°–66° C.

EXAMPLE 8

Preparation of 2-[(N-(4(R)-hydroxy-N-(3,4-dichloro)phenylcarbamoyl-D-prolyl)-L-prolyl)amino]benzoic acid

Step 1: Preparation of cis-4-benzyloxy-N-tert-butoxycarbonyl-D-proline

A solution of N-tert-butoxycarbonyl-cis-hydroxy-D-proline (3.4 g) in tetrahydrofuran (45 ml) is cooled to 0° C., benzyl bromide (20.1 g) is added, followed by portionwise addition of sodium hydride (60% dispersion in mineral oil, 1.94 g). The reaction mixture is allowed to warm to room temperature over about 2 hours, stirred overnight, diluted with ethyl acetate and water, concentrated in vacuo, and the aqueous layer washed with ether. The ether wash is back-extracted with 2N sodium hydroxide solution and the combined aqueous layers are acidified to pH 1 with 6N hydrochloric acid, then extracted with ethyl acetate. The organic solution is washed with brine, dried over magnesium sulfate, filtered, and concentrated in vacuo to give the desired product.

Step 2: Preparation of benzyl 2-aminobenzoate

A mixture of isatoic anhydride (8.54 g), benzyl alcohol (6.0 g), 4-dimethylaminopyridine (6.7 g), dimethylformamide (17 ml), triethylamine (5.28 g), and methylene chloride (160 ml) is refluxed overnight, diluted with an equal volume of ethyl acetate and washed with water, brine, and water. The organic solution is dried over magnesium sulfate, filtered, and concentrated in vacuo. The crude product is purified by flash chromatography eluting with 30% ethyl acetate in hexane to give the desired product.

Step 3: Preparation of benzyl
2-[(N-tert-butoxycarbonyl-L-prolyl)lamino]benzoate Using essentially the procedure of Example 7, Step 1, and purifying the crude product by flash chromatography eluting with 15% ethyl acetate in hexane, the desired product is prepared from benzyl 2-aminobenzoate and N-tert-butoxycarbonyl-L-proline.

Step 4: Preparation of benzyl
2-[(L-prolyl)lamino]benzoate

To a solution of benzyl 2-[(N-tert-butoxycarbonyl-L-prolyl)lamino]benzoate (0.81 g)in methylene chloride (20 ml) is added ethanedithiol (0.93 g) and trifluoroacetic acid (4.5 g) and the solution stirred at room temperature overnight. The solution is concentrated in vacuo to give the desired product as the trifluoroacetate salt.

Step 5: Preparation of benzyl
2-[(N-(4(R)-benzyloxy-N-(tert-butoxycarbonyl-D-prolyl)-L-prolyl)amino]benzoic acid A solution of cis-4-benzyloxy-N-tert-butoxycarbonyl-D-proline (0.70 g) and N-methyl morpholine (0.21 g) in methylene chloride (20 ml) is cooled to −10° C. and isopropenyl chloroformate (0.24 ml) is added dropwise. After stirring the solution for about 5 minutes, 4-dimethylaminopyridine (0.24 g) is added followed by addition of a solution of benzyl 2-[(L-prolyl)lamino]benzoate, trifluoroacetate salt (1.97 mmol) and N-methyl morpholine (0.22 g)in methylene chloride (5 ml). The mixture is stirred for about 6 hours, diluted with ethyl acetate, washed with 10% hydrochloric acid, 10% sodium carbonate, and brine. The organic solution is dried over magnesium sulfate, filtered and concentrated in vacuo. The crude product is purified by flash chromatography eluting with a gradient of 20% to 30% ethyl acetate in methylene chloride to give the desired product.

Step 6: Preparation of benzyl 2-[(N-(4(R)-benzyloxy-D-prolyl)-L-prolyl)amino]benzoic acid Using essentially the procedure of Example 8, Step 4, the desired product is prepared, as the trifluoroacetate salt, from benzyl 2-[(N-(4(R)benzyloxy-N-(tert-butoxycarbonyl-D-prolyl)-L-prolyl)amino]benzoic acid.

Step 7: Preparation of benzyl
2-[(N-(4(R)-benzyloxy-N-(3,4dichloro)phenylcarbamoyl-D-prolyl)-L-prolyl)amino]benzoate Using essentially the procedure of Example 1, Step 3, and purifying the crude product by flash chromatography, eluting with a gradient of 20% to 25% ethyl acetate in methylene chloride, the desired product is prepared from the trifluoroacetate salt of benzyl 2-[(N-(4(R)-benzyloxy-D-prolyl)-L-prolyl)amino]benzoate and 3,4-dichlorophenylisocyanate.

Step 8: Preparation of
2-[(N-(4(R)-hydroxy-N-(3,4-dichloro)phenylcarbamoyl-D-prolyl)-L-prolyl)amino]benzoic acid Using essentially the procedure of Example 7, Step 4, the desired product, m.p. 166°–169° C. is prepared from benzyl 2-[(N-(4(R)-benzyloxy-N-(3,4-dichloro)phenylcarbamoyl-D-prolyl)-L-prolyl)amino]benzoate.

EXAMPLE 9

Preparation of
2-[(N-(4(R)-benzyloxy-N-naphth-2-ylcarbamoyl-L-prolyl)-L-prolyl)amino]benzoic acid Step 1: Preparation of benzyl
2-[(N-(4(R)-benzyloxy-N-naphth-2-ylcarbamoyl-L-prolyl)-L-prolyl)amino]benzoate Using essentially the procedure of Example 1, Step 3, and purifying the crude product by flash chromatography eluting with 60% ethyl acetate in hexane, the desired product is prepared from the trifluoroacetate salt of benzyl 2-[(N-(4(R)-benzyloxy-L-prolyl)-L-prolyl)amino]benzoate and 2-naphthyl isocyanate.

Step 2: Preparation of
2-[(N-(4(R)-benzyloxy-N-naphth-2-ylcarbamoyl-L-prolyl)-L-prolyl)amino]benzoic acid Using essentially the procedure of Example 7, Step 4, the desired product, m.p. 156° C., is prepared from benzyl 2-[(N-(4(R)-benzyloxy-N-naphth-2-ylcarbamoyl-L-prolyl)-L-prolyl)amino]benzoate.

Using essentially the procedures described above, the following compounds are prepared from the appropriate starting materials.

EXAMPLE 10

2-[(N-(4(R)-benzyloxy-N-(3,4-dichloro)phenylcarbamoyl-L-prolyl)-L-prolyl)amino]benzoic acid

EXAMPLE 11

2-[(N-(4(R)benzyloxy-N-naphth-1-ylcarbamoyl-L-prolyl)-L-prolyl)amino]benzoic acid, m.p. 171° C.

EXAMPLE 12

3-[(N-(4(R)benzyloxy-N-(3,4-dichloro)phenylcarbamoyl-D-prolyl)-L-prolyl)amino]propanoic acid The compounds of the present invention are useful for treatment or prevention of cholecystokinin and gastrin related disorders of the central nervous, gastrointestinal, and appetite regulatory systems. It is believed that the compounds exhibit such utility by virtue of their ability to antagonize the actions of cholecystokinin and gastrin.

The compounds of this invention can normally be administered orally or parenterally, in the treatment of gastrin or cholecystokinin related disorders.

The compounds of this invention may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of gastrin and cholecystokinin antagonist compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, they are suitably buffered, they are made isotonic with sufficient saline or glucose and sterilized by heating or microfiltration.

The dosage regimen in carrying out the method of this invention is that which insures maximum therapeutic response until improvement is obtained and thereafter the minimum effective level which gives relief. In general, the oral dose may be between about 10 mg/kg and about 300 mg/kg, and the i.v. dose about 0.1 mg/kg to about 200 mg/kg, bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

The effectiveness of the compounds of this invention as gastrin or cholecystokinin antagonists may be determined by the following pharmacologic tests which evaluate the gastrin and cholecystokinin antagonist activity of said compounds. The CCK-A Receptor Binding Assay and the Gastrin Receptor Binding Assay are standard test procedures. The CCK-A Receptor Binding Assay is essentially that of Chang, et al., "Characterization of the Binding of [$^3$H]-($\pm$)-L-364,718: A New Potent, Nonpeptide Cholecystokinin Antagonist Radioligand Selective for Peripheral Receptors", *Molecular Pharmacology*, 30: 212–217 (1986). The Gastrin Receptor Binding Assay is essentially that of Chang, et al., "Characterization of [$^3$H]Pentagastrin Binding in Guinea Pig Gastric Glands - An Alternative Convenient Ligand for Receptor Binding Assay", *Biochemical and Biophysical Research Communications*, 134 (2): 895–899 (1986).

CCK-A Receptor Binding Assay

Materials

Wash Buffer (for use with Brandel Cell Harvester):
  30 liters (L) of 50 mM Tris, pH 7.7: Dissolve 1 81.7 g Tris base in 4 L deionized water at room temperature. Adjust pH to 7.7 with 6N HCl and Q.S. to 30 L.

Assay Buffer:
  50 mM Tris-Cl, 5 mM $MgCl_2$, 5 mM dithiothreitol, 0.14 mg/ml bacitracin, and 2 mg/ml bovine serum albumin (BSA).

1 liter of 5X stock buffer:
  30.28 g Tris base per 800 ml deionized water, 5.08 g $MgCl_2 \cdot 6H_2O$, pH to 7.7 at room temperature with 6N HCl and Q.S. to 1 liter, store at 4° C.

250 ml working buffer (kept on ice):
  50 ml of 5X stock buffer 0.1928 g dithiothreitol (5 mM), 35 mg bacitracin (0.14 mg/ml), and 0.5 g BSA (2mg/ml).

Unlabeled L-364,718 (nonpeptide ligand):
  Unlabeled L-364,718 (N-(2,3-dihydro-1-methyl-2-oxo-5-phenyl-1H-1,4-benzodiazepin-3-yl)-1H-indole-2-carboxamide) (300 nM final concentration) is used to define nonspecific binding. A 3 mM solution is made in absolute ethanol and stored at −70° C. Aliquots are diluted 100-fold in the assay.

Receptors Preparation:
  A Sprague-Dawley rat is sacrificed by asphyxiation with carbon dioxide and the pancreas removed. The tissue is immersed in cold wash buffer and carefully trimmed of fat, connective tissue, blood vessels, blotted and weighed. The tissue is homogenized in a Sorvall SS-34 centrifuge tube in 50 volumes of wash buffer using a Polytron at setting 7 for 15 seconds. The tissue is centrifuged (Sorvall SS-34) at 19,000 rpm for 10 min. The supernatant is poured off and the pellet resuspended in sufficient buffer to obtain a concentration of 40 mg tissue wet weight/ml. Separate aliquots (2.3ml) are placed in each of 8 centrifuge tubes and centrifuged as before. The supernatants are poured off and the pellets stored at −70° C. Stored pellets are sufficient for the assay of 160 tubes and are stable for 1–2 months.

During the assay the stored membranes are resuspended in 40 ml of assay buffer by scraping the pellet off the wall of the centrifuge tube and washing it into a teflon-glass homogenizer. Membranes are resuspended by 5 passes with the teflon pestle and the membranes stored on ice until ready for use.

Preparation of Compounds:
  Compounds of the present invention to be tested are prepared in DMSO (dimethyl sulfoxide) or in assay buffer. The majority of compounds of the present invention active as CCK antagonists generally require DMSO for complete solubility. Approximately 2–3 mg of compound is weighed directly into a 13×100 mm test tube and sufficient DMSO added to obtain a working stock solution at a concentration 100 fold greater than the highest concentration being tested in the assay. A total of 10 µl of each concentration of drug is added into a final volume of 1 ml to yield a 100 fold dilution of the working stock solution. Control binding tubes ("totals and nonspecifics") are also treated with 10 µl DMSO.

Radioligand Preparation:
  $^3$H-L-364,718 is obtained from New England Nuclear (Cat. #971) and is used as supplied. The final assay concentration of $^3$H-L-364,718 in assay buffer should be 0.2 nM in a final assay volume of 1 ml. $^3$H-L-364,718 (0.2 pmol) is added into the assay in a volume of 25 µl (8 nM working stock solution). The required dilution (usually >1000 fold) is obtained by dividing the working stock concentration into the concentration of the specific lot of $^3$H-L364,718.

Assay Procedure

Samples are prepared in triplicate and a "total" (buffer addition) and "nonspecific" (300 nM unlabeled L-364,718) set of tubes included in each set of 24 tubes. The "total" assay tubes contain 25 μl $^3$H-L-364,718 solution, 250 μl membrane suspension, 10 μl DMSO and 715 μl assay buffer. The "nonspecific" assay tubes contain 25 μl $^3$H-L-364,718 solution, 10 μl unlabeled L-364,718 solution, 250 μl membrane suspension, 10 μl DMSO, and 705 μl assay buffer. The remaining 6 sets of triplicates are used either for screening or IC$_{50}$ determinations. These tubes contain 25 μl $^3$H-L-364,718 solution, 250 μl membrane suspension, 10 μl of a solution of the compound of the present invention to be tested, and 715 μl assay buffer. The order of addition is compound of the present invention-DMSO, buffer, unlabeled L-364,718, $^3$H-L364,718, and, to start the assay, membrane suspension.

While tubes are incubating in a shaking water bath at 37° C. for 30 minutes, Brandel deposit/dispense filters are presoaked in wash buffer. Following the end of the incubation, sets of 24 tubes are rapidly washed with assay buffer as follows. Assay buffer is added to the incubation tubes to the height of the uppermost cross support in the standard Brandel test tube rack and the contents immediately aspirated. This process is repeated twice more, the filter removed, marked and the next set of 24 tubes processed. It is critical that the filtration-washing step be completed as quickly as possible; preferably within 20 seconds. The individual filter rings from a single filter strip are dispensed into 7 ml minivials and 5 ml of scintillation cocktail (AquaSol 2, Dupont) added using the Brandel deposit/dispenser apparatus. Samples are counted following either 30 minutes of low speed shaking on a horizontal shaker (Eberbach Corp.) or a prolonged equilibration period (>2 hr) in the scintillation counter (Beckman model 6000 IC).

For screening studies, or in the determination of IC$_{50}$ values, results are expressed as the degree of inhibition of specific binding by the addition of a compound of the present invention. Specific binding is defined as the difference between the counts from "total" and "nonspecific" tubes. The nonspecific binding value is also subtracted from each sample and the specific binding expressed as a percentage of that seen in the absence of a compound of the present invention. For screening (usually at 100 μM) the percent of specific binding is the desired quantity, whereas for determination of the IC$_{50}$ concentration, one tests multiple concentrations of compounds of the present invention to define the concentration at which specific binding is reduced 50%.

Gastrin Receptor Binding Assay

Preparation of Glands
Solutions:

Phosphate Buffered Saline (PBS): 8.743 g NaCl, 523 mg K$_2$HPO$_4$ and 76.8 mg NaH$_2$PO$_4$ is dissolved in 900 ml of deionized water, the pH of the solution is adjusted to 7.3 with 5N NaOH, then Q.S. to 1 L.

Buffer A: Powdered Basal Medium Eagle (BME) containing Earle's Salts, L-glutamine and 25 mM HEPES without bicarbonate (Sigma Cat. number B 4391) sufficient to make 3 liters is stirred into 2.7 L of deionized water, 6.6 mg sodium bicarbonate is added and the mixture stirred to give dissolution. The solution is then equilibrated with 95% O$_2$/5% CO$_2$ gas followed by titration to a pH of 7.4 with NaOH, then Q.S. to 3 L.

Buffer B: 18.75 mg of collagenase A and 25 mg of pH neutralized BSA is dissolved in 25 ml of Buffer A.

Buffer C: 0.3 g of BSA is dissolved in 300 ml of Buffer A.

Buffer D: 6.25 mg Bacitracin is dissolved in 25 ml of Buffer A.

Method:

A guinea pig (Hartley Strain) weighing 150-200 grams, is sacrificed by CO$_2$ asphyxiation and the stomach immediately excised, cut along the greater curvature, cleaned out and immediately immersed in a beaker containing cold PBS, pH 7.3, to insure thorough cleaning. The fundic mucosa is gently scraped off the submucosa and added to a preweighed 50 ml plastic centrifuge tube containing 30 ml of cold Buffer A. The weight of the plastic centrifuge tube containing the buffer is then subtracted from the combined weight of the mucosa and the buffer-containing tube to give the weight of the mucosa. The weight of the mucosa thus determined is recorded for later calculations. The mucosa is then washed twice in Buffer A. After the final wash, the tissue is minced and is placed in a 100-ml glass beaker containing about 1.0 ml of Buffer A, and washed twice again by repeated centrifugation at 50Xg for 5 minutes each and aspiration of supernatant. The washed tissue fragments are then added to a glass Erlenmeyer flask containing 25 ml of Buffer B and incubated in a Dubnoff shaking water bath at 37° C. for 30 minutes in a 95% O$_2$/5% CO$_2$ atmosphere. After the incubation, the digested tissue fragments in the Collegenase-buffer solution are triturated, filtered through a 200-micron nylon mesh and centrifuged at 50Xg for 5 minutes. The supernatant is aspirated and discarded, the tissue washed 2X in Buffer C, resuspended in same buffer, incubated in a 37° C water bath in an atmosphere of 95% O$_2$/5% CO$_2$ for 5 minutes, and centrifuged. The pelleted glands are suspended in Buffer D at a desired concentration of $2\times10^5$ glands/ml to use in the receptor binding assay.

Assay Method

Assay Buffer: Buffer A as above
Ligand Solutions:

$^{125}$I-(Leu-15)-Gastrin: 100 microcurie dissolved in 2.0 ml of Buffer A to make 50 microcurie/ml; stored in 50 μl aliquots under Argon at −70° C.

$^{125}$I-(15-methionine)-Human Gastrin: 50 microcurie/ml in deionized water, stored in 50 μl aliquots as above.

(Leu 15)-Gastrin 17:5.2 mg of (Leu-15)- Gastrin is dissolved in 10 ml of Buffer A and stored in 30 μl aliquots. At the time of assay a 1:10 dilution is made and 10 μl/assay tube is used.

Method:

Six minisorp tubes (16×100 mm) are serially marked and divided into two groups thus: tubes #1, #2, and #3 are marked "T" for "Totals" and tubes #4, #5, and #6 are marked "NS" for "Non-Specifics." Into each of the six tubes are added 220 μl of prepared glands in Buffer D; 20 μl of Buffer A in tubes #1, #2, and #3; 10 μl, in tubes #4, #5 and #6; (10 μl of (Leu-15)-Gastrin (25 μM) in tubes #4, #5, and #6. The six tubes are then transferred immediately to a 25° C. water bath and challenged each with 10 μl 125I-(Leu-15)-Gastrin diluted as per calculation. The tubes are then covered with a gas hood connected to a 95% O$_2$/5% CO$_2$ gas source and mechanically agitated in a shaker for 30 minutes.

At the end of the incubation period, the assay mixtures are each filtered through a Whatman glass fiber filter B on a Brandel tissue harvester and washed twice with Buffer A. The filters are pre-soaked in Buffer C before use. The filter strips are removed after the final wash and individual filters counted in a Gamma Counter. The counts from the "Non-Specific" tubes are then averaged and subtracted from the average "Totals" to give the Specific Counts.

For screening compounds, the above assay method is utilized except that triplicate tubes are prepared for each concentration of compound of the present invention to be assayed. 20 μl of a solution of each compound to be assayed in triplicate are added to each designated tube.

In displacement studies the $IC_{50}$ value is the concentration of compound causing a 50% decrease in specific binding of a tracer amount of $^{125}I$-(Leu-15) Gastrin. The $IC_{50}$ value is derived from a plot of the log of the displacer concentration against the percentage of specific binding.

Compounds of the present invention exhibit marked activity in the foregoing tests and are considered useful for treatment or prevention of cholecystokinin and gastrin related disorders. Results of testing of compounds of the present invention by the above methods are presented in the table below.

| In Vitro Binding Data | | |
|---|---|---|
| | $IC_{50}$ (μM) | |
| Compound of Example | CCK-A | Gastrin |
| 1 | 9 | >300 |
| 2 | 15 | 120 |
| 3 | 30 | >300 |
| 4 | 7.3 | 10.3 |
| 5 | 37 | >30 |
| 6 | 37 | >30 |
| 7 | 3 | 2.6 |
| 9 | | 0.13 |
| 11 | | 0.20 |

What is claimed is:

1. A method of preventing in a mammal, or treating a mammal for, cholecystokinin or gastrin-related disorders of the gastrointestinal, central nervous or appetite regulatory systems which comprises administering to said mammal a therapeutically effective amount of a compound of the formula

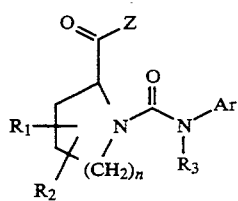

wherein:

Ar is aryl;

$R_1$ and $R_2$ are independently hydrogen, alkyl, aryl, aralkyl, hydroxy, alkoxy, aryloxy, aralkoxy, halo, —$NR_4R_5$ where $R_4$ and $R_5$ are independently hydrogen, alkyl, aralkyl, or aryl, or when $R_1$ and $R_2$ are vicinal, $R_1$ and $R_2$ may be taken together to be

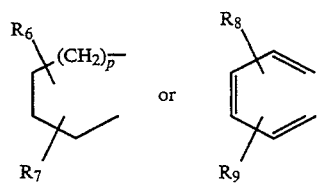

where $R_6$ and $R_7$ are independently hydrogen, alkyl, aryl, aralkyl, hydroxy, alkoxy, aryloxy, aralkoxy, or halo, and $R_8$ and $R_9$ are independently hydrogen, or an aryl group substituent, and p is 0, 1, or 2;

$R_3$ is hydrogen or alkyl;

Z is unsubstituted or substituted nitrogen-containing heterocyclyl, —$NR_aR_b$ where $R_a$ and $R_b$ are independently hydrogen, alkyl, aryl, aralkyl, or when taken together, $R_a$ and $R_b$ may form —$(CH_2)_t$— where t is 3, 4, or 5,

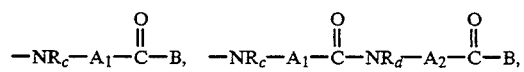

where $A_1$ and $A_2$ are independently alkylene, phenylene, cycloalkylene, arylalkylene, arylalkylalkylene, alkoxycarbonylalkylalkylene, aryloxycarbonylalkylalkylene, aralkoxycarbonylalkylalkylene, carboxyalkylalkylene, carbamoylalkylalkylene, alkylthioalkylalkylene, hydroxymethylmethylene, (1-hydroxyethyl)methylene, (4hydroxyphenyl)methylmethylene, indol-3-ylmethylmethylene, imidazol-4-ylmethylmethylene, guanidinoalkylalkylene, or aminoalkylalkylene, B is hydroxy, alkoxy, aralkoxy, aryloxy or —$NR_fR_g$ where $R_f$ and $R_g$ are independently hydrogen, alkyl, aralkyl, carboxyalkyl, alkoxycarbonylalkyl, aryloxycarbonylalkyl or aralkoxycarbonylalkyl, and $R_c$ and $R_d$ are independently hydrogen, alkyl, aryl, or aralkyl, —$NR_c$-$A_1$— may be

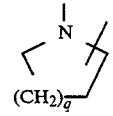

where q is 0, 1, 2, or 3, and —$NR_d$-$A_2$— may be

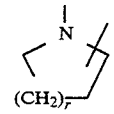

where r is 0, 1, 2, or 3; and n is 0, 1, 2, or 3;

or a pharmaceutically acceptable salt thereof.

2. A method of preventing in a mammal, or treating a mammal for, cholecystokinin or gastrin-related disorders of the gastrointestinal, central nervous or appetite regulatory systems which comprises administering to said mammal a therapeutically effective amount of a compound of the formula

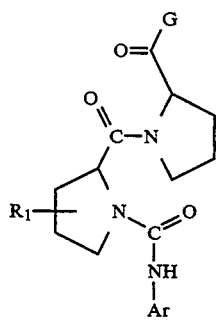

wherein
Ar is aryl;
r is 0, 1, 2 or 3;
$R_1$ is substituted or unsubstituted aralkoxy; and
G is

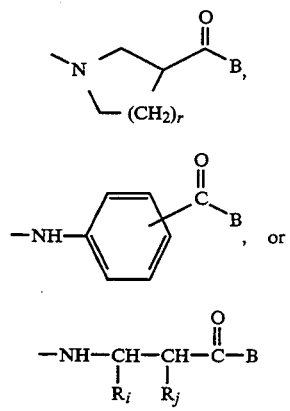

where
r is 0, 1, 2, or 3;
B is hydroxy, alkoxy, aralkoxy, aryloxy or —$NR_fR_g$ where $R_f$ and $R_g$ are independently hydrogen, alkyl, or aralkyl, and
$R_i$ and $R_j$ are independently hydrogen, alkyl, or $R_i$ and $R_j$ may be taken together to be —$(CH_2)_u$— where u is 2, 3, 4, or 5; in a pharmaceutically acceptable salt thereof.

3. A method of preventing in a mammal, or treating a mammal for, cholecystokinin or gastrin-related disorders of the gastrointestinal, central nervous or appetite regulatory systems which comprises administering to said mammal a therapeutically effective amount of a pharmaceutical composition comprising a therapeutically effective amount for antagonism of the function of cholecystokinins or gastrin in a mammal of a compound of the formula

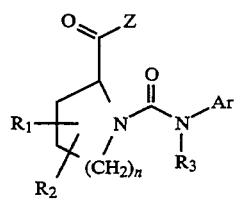

wherein:
Ar is aryl;

$R_1$ and $R_2$ are independently hydrogen, alkyl, aryl, aralkyl, hydroxy, alkoxy, aryloxy, aralkoxy, halo, —$NR_4R_5$ where $R_4$ and $R_5$ are independently hydrogen, alkyl, aralkyl, or aryl, or when $R_1$ and $R_2$ are vicinal, $R_1$ and $R_2$ may be taken together to be

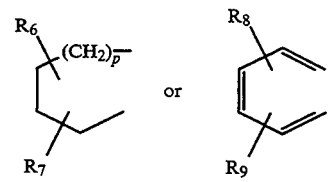

where $R_6$ and $R_7$ are independently hydrogen, alkyl, aryl, aralkyl, hydroxy, alkoxy, aryloxy, aralkoxy, or halo, and
$R_8$ and $R_9$ are independently hydrogen, or an aryl group substituent,
and p is 0, 1, or 2;
$R_3$ is hydrogen or alkyl;
Z is unsubstituted or substituted nitrogen-containing heterocyclyl, —$NR_aR_b$ $R_b$ where $R_a$ and $R_b$ are independently hydrogen, alkyl, aryl, aralkyl, or when taken together, $R_a$ and $R_b$ may form —$(CH_2)_t$— where t is 3, 4, or 5,

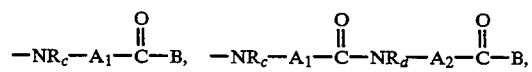

where
$A_1$ and $A_2$ are independently alkylene, phenylene, cycloalkylene, arylalkylene, arylalkylalkylene, alkoxycarbonylalkylalkylene, aryloxycarbonylalkylalkylene, aralkoxycarbonylalkylalkylene, carboxyalkylalkylene, carbamoylalkylalkylene, alkylthioalkylalkylene, hydroxymethylmethylene, (1-hydroxyethyl)methylene, (4-hydroxyphenyl)methylmethylene, indol-3-ylmethylmethylene, imidazol-4-ylmethylmethylene, guanidinoalkylalkylene, or aminoalkylalkylene,
B is hydroxy, alkoxy, aralkoxy, aryloxy or —$NR_fR_g$ where $R_f$ and $R_g$ are independently hydrogen, alkyl, aralkyl, carboxyalkyl, alkoxycarbonylalkyl, aryloxycarbonylalkyl or aralkoxycarbonylalkyl, and
$R_c$ and $R_d$ are independently hydrogen, alkyl, aryl, or aralkyl, —$NR_c$-$A_1$— may be

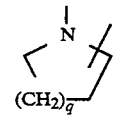

where q is 0, 1, 2, or 3; and —$NR_d$-$A_2$— may be

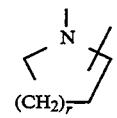

where r is 0, 1, 2, or 3; and n is 0, 1, 2, or 3;

or a pharmaceutically acceptable salt thereof, and a pharmaceutically acceptable carrier.

4. A method according to claim 1 wherein $R_1$ and $R_2$ are vicinal and are taken together to be

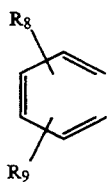

where $R_8$ and $R_9$ are independently hydrogen, or an aryl group substituent.

5. A method according to claim 1 wherein $R_1$ and $R_2$ are vicinal and are taken together to be

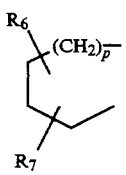

where $R_6$ and $R_7$ are independently hydrogen, alkyl, aryl, aralkyl, hydroxy, alkoxy, aryloxy, aralkoxy, or halo, and p is 0, 1, or 2.

6. A method according to claim 1 wherein

Z is unsubstituted or substituted nitrogen-containing heterocyclyl.

7. A method according to claim 1 wherein Z is

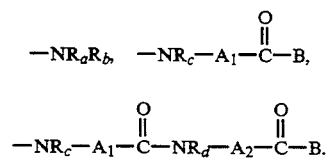

8. A method according to claim 1 wherein said compound is 2-[(N-(3-methyl)phenylcarbamoyl-4(R)-benzyloxy)-L-prolyl]-1,2,3,4-tetrahydro-9H-pyrido[3,4-b]indole or a pharmaceutically acceptable salt thereof.

9. A method according to claim 1 wherein said compound is 2-[(N-(4-methoxy)phenylcarbamoyl-4(R)-benzyloxy)-L-prolyl]- 1,2,3,4-tetrahydro-9H-pyrido[3,4-b]indole or a pharmaceutically acceptable salt thereof.

10. A method according to claim 1 wherein said compound is 2-[(N-(3-methyl)phenylcarbamoylindolin-(S)-yl)carbonyl]-1,2,3,4-tetrahydro-9H-pyrido[3,4-b]indole or a pharmaceutically acceptable salt thereof.

11. A method according to claim 1 wherein said compound is 2-(N-naphth-2-ylcarbamoyl-D-prolyl)1,2,3,4-tetrahydro-9H-pyrido[3,4-b]indole or a pharmaceutically acceptable salt thereof.

12. A method according to claim 1 wherein said compound is 2-[N-(3-methyl)phenylcarbamoyl-D-prolyl)-1,2,3,4-tetrahydro-9H-pyrido[3,4-b]indole or a pharmaceutically acceptable salt thereof.

13. A method according to claim 1 wherein said compound is 2-[N-(3-methyl)phenylcarbamoyl-L-prolyl]1,2,3,4-tetrahydro-9H-pyrido[3,4-b]indole or a pharmaceutically acceptable salt thereof.

14. A method according to claim 1 wherein said compound is N-[4(R)-benzyloxy-N-(3-methyl)phenylcarbamoyl)-L-prolyl]-D-leucyl-D-aspartic acid amide or a pharmaceutically acceptable salt thereof.

15. A method according to claim 1 wherein said compound is 2-[(N-(4(R)-hydroxy-N-(3,4-dichloro)phenylcarbamoyl-D-prolyl)-L-prolyl)amino]benzoic acid or a pharmaceutically acceptable salt thereof.

16. A method according to claim 1 wherein said compound is 2-[(N-(4(R)-benzyloxy-N-naphth-2-ylcarbamoyl-L-prolyl)-L-prolyl)amino]benzoic acid or a pharmaceutically acceptable salt thereof.

17. A method according to claim 1 wherein said compound is 2-[(N-(4(R)-benzyloxy-N-(3,4-dichloro)-phenylcarbamoyl-L-prolyl)-L-prolyl)amino]benzoic acid or a pharmaceutically acceptable salt thereof.

18. A method according to claim 1 wherein said compound is 2-[(N-(4(R)benzyloxy-N-naphth-1-ylcarbamoyl-L-prolyl)-L-prolyl)amino]benzoic acid or a pharmaceutically acceptable salt thereof.

19. A method according to claim 1 wherein said compound is 3-[(N-(4(R)benzyloxy-N-(3,4-dichloro)phenylcarbamoyl-D-prolyl)-L-prolyl)amino]propanoic acid or a pharmaceutically acceptable salt thereof.

* * * * *